United States Patent
Wildemeersch (10) Patent No.: US 11,672,691 B2
(45) Date of Patent: Jun. 13, 2023

(54) INSTRUMENT FOR THE INSERTION OF A BIOACTIVE FRAMELESS OR FRAMED INTRAUTERINE DEVICE OR INTRAUTERINE SYSTEM THROUGH A HYSTEROSCOPE

(71) Applicant: PAT & Co bvba, Lichtervelde (BE)

(72) Inventor: Dirk Wildemeersch, Ghent (BE)

(73) Assignee: PAT & CO BVBA, Lichtervelde (BE)

( * ) Notice: Subject to any disclaimer, the term of this patent is extended or adjusted under 35 U.S.C. 154(b) by 508 days.

(21) Appl. No.: 15/750,596

(22) PCT Filed: Aug. 8, 2016

(86) PCT No.: PCT/EP2016/068871
§ 371 (c)(1),
(2) Date: Feb. 6, 2018

(87) PCT Pub. No.: WO2017/025502
PCT Pub. Date: Feb. 16, 2017

(65) Prior Publication Data
US 2019/0015247 A1    Jan. 17, 2019

(30) Foreign Application Priority Data
Aug. 7, 2015 (EP) ..................................... 15180188

(51) Int. Cl.
*A61F 6/18* (2006.01)
*A61F 6/14* (2006.01)
(52) U.S. Cl.
CPC .................. *A61F 6/18* (2013.01); *A61F 6/14* (2013.01); *A61F 6/142* (2013.01); *A61F 6/144* (2013.01)
(58) Field of Classification Search
CPC ...... A61F 6/00; A61F 6/06; A61F 6/08; A61F 6/12; A61F 6/14; A61F 6/142;
(Continued)

(56) References Cited

U.S. PATENT DOCUMENTS 3,635,215 A * 1/1972 Shea .......................... A61F 6/18
128/840
3,777,748 A * 12/1973 Abramson .............. A61F 6/142
128/840
(Continued)

FOREIGN PATENT DOCUMENTS

CN          1380047 A      11/2002
DE          19815552 C1     9/1999
(Continued)

OTHER PUBLICATIONS

Bard. Bard MAX-CORE Disposable Core Biopsy Instrument. CR Bard. https://www.crbard.com/Biopsy/en-US/Products/BARD-MAX-CORE-Disposable-Core-Biopsy-Instrument-Ba. Published 2018. Accessed Apr. 24, 2020 (Year: 2018).*
(Continued)

*Primary Examiner* — Michelle J Lee
(74) *Attorney, Agent, or Firm* — The Webb Law Firm (57) ABSTRACT

A disposable IUD/IUS inserter is for use in conjunction with a hysteroscope, or blindly, including an inner part which has a flexible metal inner tube, between 1 and 2 mm in diameter. The inner tube has a front end portion including a stylet, the stylet being less than 1 mm in diameter, and the stylet being provided with a stylet tip. The IUD/IUS inserter is further provided with a handle at a rear end of the inner tube, a handle unlocking mechanism for positioning of an IUD or IUS, a release mechanism for releasing of a tail of the IUD/IUS, and an outer tube sized to allow passage through a hysteroscope working channel, the handle unlocking mechanism being connected to the outer tube.

12 Claims, 5 Drawing Sheets

(58) Field of Classification Search
CPC .. A61F 6/144; A61F 6/146; A61F 6/16; A61F 6/18; A61F 6/22; A61F 6/225; A61F 2006/045; A61F 2006/046; A61F 2006/048; A61F 13/20; A61F 13/2002; A61F 13/2011; A61F 13/34; A61F 2013/2014; A61F 2/1664; A61F 2/1662; A61F 2/1667; A61F 2/167; A61F 2/1672; A61F 2/1675; A61F 2/1678; A61F 13/26–266; A61M 2205/02; A61M 2205/0238; A61M 2205/586; A61M 2210/14; A61M 2210/1433; A61M 2205/00–0205; A61M 2205/58
See application file for complete search history.

(56) References Cited

U.S. PATENT DOCUMENTS

| | | | |
|---|---|---|---|
| 3,857,391 A | 12/1974 | Lerner | |
| 4,582,052 A * | 4/1986 | Dunn | A61K 9/0039 424/432 |
| 4,708,134 A | 11/1987 | Wildemeersch | |
| 4,949,732 A * | 8/1990 | Spoon | A61F 6/18 128/839 |
| 5,433,218 A | 7/1995 | Wildemeersch | |
| 5,685,864 A * | 11/1997 | Shanley | A61B 5/150244 604/207 |
| 5,785,053 A * | 7/1998 | Macandrew | A61F 6/18 606/119 |
| 7,621,276 B2 * | 11/2009 | Tal | A61F 6/144 128/830 |
| 9,949,870 B2 | 4/2018 | Frankenne et al. | |
| 2006/0293560 A1 * | 12/2006 | Nguyen | A61F 6/06 600/104 |
| 2013/0014762 A1 * | 1/2013 | Deckman | A61F 6/144 128/833 |
| 2013/0213406 A1 * | 8/2013 | Frankenne | A61F 6/18 128/830 |
| 2014/0128345 A1 * | 5/2014 | Woodrow | A61K 31/7072 514/304 |
| 2015/0202076 A1 * | 7/2015 | Wijzen | A61F 6/18 128/833 |
| 2016/0270846 A1 * | 9/2016 | Truckai | A61F 6/22 |
| 2017/0056237 A1 * | 3/2017 | Tal | A61M 31/00 |
| 2017/0273716 A1 * | 9/2017 | Garofalo | A61B 1/307 |

FOREIGN PATENT DOCUMENTS

| | | |
|---|---|---|
| EP | 0191747 A1 | 8/1986 |
| EP | 0445150 B1 | 9/1992 |
| WO | 2012055766 A2 | 5/2012 |

OTHER PUBLICATIONS

Medical Device Database [database online]. District of Columbia. U.S. Food and Drug Administration; Feb. 21, 2014. https://www.accessdata.fda.gov/scripts/cdrh/cfdocs/cfpmn/pmn.cfm?ID=K133948. Accessed Apr. 24, 2020 (Year: 2014).*

Bard. Bard MAX-CORE Disposable Core Biopsy Instrument. CR Bard. https://www.crbard.com/Biopsy/en-US/Products/BARD-MAX-CORE-Disposable-Core-Biopsy-Instrument-Ba. Published 2018. Accessed Apr. 24, 2020 (Year: 2014).*

Wildemeersch, et al., "L'implant contraceptif intra-utérin sans armature", Gynécol Obstét Fertil, 2001, pp. 549-564, vol. 29 (relevant for reasons listed on p. 3 of the specification).

* cited by examiner

INSTRUMENT FOR THE INSERTION OF A BIOACTIVE FRAMELESS OR FRAMED INTRAUTERINE DEVICE OR INTRAUTERINE SYSTEM THROUGH A HYSTEROSCOPE

CROSS-REFERENCE TO RELATED APPLICATIONS

This application is the United States national phase of International Application No. PCT/EP2016/068871 filed Aug. 8, 2016, and claims priority to European Patent Application No. 15180188.3 filed Aug. 7, 2015, the disclosures of which are hereby incorporated in their entirety by reference.

FIELD AND BACKGROUND OF THE INVENTION

The challenge of intrauterine contraceptive researchers, is to develop ideal, short or long-term, intrauterine contraceptive devices (IUD) or intrauterine contraceptive systems IUS) which have the following attributes:

Single or multipurpose methods that prevent pregnancy effectively, are well tolerated, do not become displaced or expelled, are long-lasting, have a strictly local effect, do not cause menstrual disturbances, prevent sexually transmitted infection (STI), are easy to insert and remove, are relatively cheap, and which can be applied with the aid of visual insertion such as by hysteroscopy to provide precision insertion. The latter is paramount. In order to obtain optimal results, even the most simple insertion technique should be done with skill. Proper training for skillful IUD insertion has sometimes been overlooked in the past but is essential to obtain optimal results. One of the consequences of lack of proper training is the greater chance of incorrect insertion with subsequent increase in problems leading to a poor image of the IUD and underuse of the method.

Despite the fact that the insertion of an IUD can be taught with the use of training models, insertion of all current IUDs is a blind procedure therefore subject to uncertainty with respect to placement or fit. Hysteroscopy is the inspection of the uterine cavity by endoscopy with access through the cervix. It allows for the diagnosis of intrauterine pathology and serves as a method for surgical intervention (operative hysteroscopy). A hysteroscope is an endoscope that carries optical and light channels or fibers. It is introduced in a sheath that provides an inflow and outflow channel for insufflation of the uterine cavity, allowing inspection of the uterine cavity. Hysteroscopic techniques have expanded drastically over the last decades as better equipment has become available. Both laparoscopy and hysteroscopy are techniques using direct vision for diagnostic and therapeutic purposes. Hysteroscopy, as it uses the natural entry to the uterine cavity, is generally a low risk technique. Refinement of optical and fiberoptic light instrumentation and of operative accessories allow high resolution and excellent visual documentation by hysteroscopy. Also the diameter of the instruments has become thinner so that diagnostic procedures can now be done without general anesthesia and in the office. Even minimally invasive techniques can be performed with local anesthesia and/or sedation. Although many hysteroscopic techniques have been developed, an intrauterine device (IUD) or an intrauterine system (IUS) has never been inserted using hysteroscopy.

In order to optimize the proper placement of a contraceptive device, hysteroscopic insertion is currently the most optimal way to achieve this goal. In addition, gynecologists prefer to conduct minimally invasive procedures under direct vision, as it is less likely to make mistakes and cause harm, in contrast with blind insertion, especially of framed IUDs. Congenital or acquired anomalies of the uterus are difficult to visualize in routine clinical practice. Legal liability also plays a major role in certain countries like the US and Europe. Hysteroscopic inspection prior to IUD/IUS insertion can easily diagnose congenital or acquired anomalies. Furthermore, precision intrauterine contraception could be developed by placing the active agent under direct vision close to or even in the Fallopian tube, similar to female tubal sterilization. Also very small devices could be developed which avoid the incompatibility problems mentioned above, including for use in women with congenital or acquired anomalies of the uterus.

Several hysteroscopic methods have already been developed for tubal sterilization. Hysteroscopic insertion of devices directly within the fallopian tube to block migration of sperm and/or egg have been developed as an alternative to surgical sterilization however none have been utilized for the placement of IUD given size limitations of conventional T-shape designs. The use of frameless IUDs is the first to be able to be inserted hysteroscopically.

Although sterilization is intended to be permanent, patient regret is not rare. Regret is often caused by unpredictable life conditions and occurs mainly in the younger age-groups. In a review study, regrets were expressed by over 20% of women aged 30 years or younger and by 6% of women older than 30 years. Therefore, the option of reversible method contraception equivalent in efficacy to tubal ligation will be attractive to many women. One study provided data which indicate that the availability of a reversible method of sterilization would significantly increase the acceptability of the method to potential candidates.

It is known that copper ions, in the upper part of the uterine cavity, causes a foreign body reaction widespread throughout the genital tract, including the fallopian tubes. Copper ions, together with products derived from the inflammatory reaction present in the luminal fluids of the genital tract, are toxic for spermatozoa and oocytes, preventing the encounter of healthy gametes and the formation of viable embryos.

Hormone-releasing intrauterine systems are well-known and have been developed for contraceptive purposes and for the treatment of various gynecological conditions such as heavy menstrual bleeding or menorrhagia. They act by suppressing the lining (endometrium) of the uterus, or by thickening the cervical mucus, so that sperm cannot reach the oviducts. These systems are therefore anti-fertility agents as they act prior to fertilization.

Copper tubes and drug delivery systems can be permanently fixed in the fundus of the uterus between the orifices of the fallopian tubes. Such a fixation method was developed for the GyneFix® IUD (Contrel Research, Ghent, Belgium; Gynecol Obstet Fert 2001; 29:549-64).

The main features of the GyneFix® IUD are that it is frameless, flexible and fixed to the fundus of the uterus. The frameless IUD was first described in 1985 (priority application BE 214449; EP 0 191 747). Unlike conventional copper IUDs where a copper wire is wrapped around a central plastic core, GyneFix® utilizes several copper cylinders, threaded on non-absorbable surgical suture material as an effective means of producing efficient copper release while allowing for a reduction in the overall shape and size of the IUD itself. It is inserted using a specially designed inserter in the office of the doctor like a conventional, framed IUD. As the method is different than the insertion procedure of conventional IUDs, doctors need to be trained in the proper insertion technique which can be cumbersome and a costly effort. Moreover, as the insertion of the anchor is done blindly, inadequate placement is a fear of many inexperienced practitioners. The advantage of frameless IUDs/IUSs is that they could be inserted through the working channel of the hysteroscope, as they are thin, and fixed under direct vision to the uterine wall in the fundus of the uterus. This would maximize insertion which would have significant benefits to women. However, as the working channel of the newer office hysteroscopes are narrow, to reduce insertion pain, the IUD/IUS should be adapted to conform to the diameter of the working channel in order to allow the technique to be applied as an office procedure.

At the time of the development of the frameless copper-releasing IUD, it was not known that the size of such a copper-releasing intrauterine device (IUD), could be reduced without affecting the effectiveness of the device. This research also found that dissolution of copper occurs from both the outside and inside of the copper cylinders of the frameless GyneFix® IUD. Recent clinical studies also found that a reduced size had a significant impact on the amount of menstrual blood loss (MBL), due to the smaller surface area of the device, without reducing the effectiveness of the IUD. Additional in vivo research on GyneFix® devices, conducted up to 12 years after placement, revealed the long duration of action of the GyneFix® IUD. Previous in vitro dissolution studies of the GyneFix® 330 IUD yielded a minimal dissolution rate, per copper tube, of 2.4 mg per year. This, in turn, confirms dissolution studies conducted with other copper IUDs which showed that copper is released constantly for long periods of time. These studies concluded that the estimation of the useful life-span of a copper-releasing IUD can be conducted on the basis of measurements of the copper weight, which is a linear, negative function of duration of use. Still other studies demonstrated the possibility of insertion of frameless copper releasing IUDs in the uterus of women through a hysteroscope by minimizing the size of the IUD. The procedure takes advantage of the small size, unique shape and novel anchoring mechanism associated with the frameless design over other conventional designs.

As both the location of the copper in the uterine cavity and the design of the copper elements are important, a copper-releasing IUD could be designed that fits in the narrow working channel of the hysteroscope which can then be anchored under vision in the fundus of the uterus in the middle or on both sides of the fundus, close to the orifices of the Fallopian tubes to prevent fertilization.

Similarly, in 1988, EP 0 445 150 described an improved intrauterine device which is a deformable element in the form of a plastic fiber releasing a substance which is active in the uterine cavity, the fiber consisting of a plurality of strands or loops held together in an assembly zone. The device carries a securing element for hooking it to the tissue of the uterus. The device was developed to be applicable for contraception and for treatment of the uterus using the same type of inserter as used for the GyneFix® IUD. Since this development, it has been shown that sufficient active contraceptive substance (hormone) can be released from a very thin fiber.

Another technique for releasing ions from metals such as copper, silver or gold, is by using micro or nanoparticles that are embedded in electrospun nano- or microfibers. The increase in incidence of drug resistance among pathogenic bacteria and viruses has made the search for new antimicrobials inevitable. In the current situation, one of the most promising and novel therapeutic agents are the nanoparticles or microparticles. The unique physiochemical properties of the nanoparticles combined with the growth inhibitory capacity against microbes has led to the upsurge in the research on nanoparticles and their potential application as antimicrobials. Metallic nanoparticles or microparticles such as copper, aluminium, gold, silver, magnesium, zinc and titanium nanoparticles can be used for local ion delivery in body organs. The potential application of nanoparticles has been reviewed recently. The application of nanoparticles as antimicrobials is gaining relevance in the medical field for prophylaxis and therapy.

Silver nanoparticles have proven to exert antiviral activity against HIV-1 at non-cytotoxic concentrations. Silver nanoparticles exert anti-HIV activity at an early stage of viral replication, most likely as a virucidal agent or as an inhibitor of viral entry. Besides, silver nanoparticles inhibit post-entry stages of the HIV-1 life cycle. These properties make them a broad-spectrum agent not prone to inducing resistance that could be used preventively against a wide variety of circulating HIV-1 strains.

Ag—Cu may be more potent to inactivate HIV-1. Ag—Cu mixed alloy nanoparticles strongly inhibit HIV-1 replication and, at limited concentrations, are relatively benign with limited toxicity to human cells. Ag and Cu ions are known to denature proteins of the target cell or organism by binding to reactive groups resulting in their precipitation and inactivation. The results of studies indicate that the broad antiviral mechanisms of Ag and Cu are extended to HIV-1 inhibition.

Ag and Cu ions can also be used for pregnancy prevention. The mechanism of action of copper ions from solid copper IUDs is well-known. The advantage of using ions from micro- or nanoparticles is their large surface area as the particles are very small but the quantity huge.

SUMMARY OF THE INVENTION

The present invention relates to a new, specially designed instrument for insertion, under vision, of a frameless IUD/IUS in the uterus close to the oviducts.

The purpose of the present invention is provide for precision intrauterine contraception and/or intrauterine treatment of gynecological conditions combining a frameless copper-releasing device, consisting of solid copper tubes, or drug releasing fibers which release hormones or copper and/or silver ions delivered from micro or nanoparticles embedded in polymers, or fibers coated with electrospun polymers loaded with micro and/or nanoparticles.

The invention is described as an office procedure which usually can be performed under local anesthesia or even without anesthesia. The challenge of the invention was to find a solution to make it possible to insert an IUD/IUS through the working channel of the office hysteroscope of limited size so that the procedure can be done in the office, with or without local anesthesia, under direct vision, allowing precision insertion.

Hysteroscopic insertion of drug releasing devices is not solely restricted to the uterus or to gynecological disorders. Such a modus operandi could also be used to treat diseases and disorders of other organ systems, such as the esophagus, bladder, gastrointestinal tract, rectum, pulmonary and cardiovascular systems. The use of hysteroscopic or other scope variations where a similar size or greater working channel is utilized would be candidates for use of drug releasing fibers similar in design to those outlined here.

The present invention is directed to an instrument, an applicator or device-inserter, for the insertion and suspension of a copper-releasing IUD or a hormone-releasing IUS. This purpose is achieved by designing a suitable instrument which, when loaded together with the IUD or IUS, can be used in the narrow channel of an office hysteroscope.

The invention relates to a hysteroscopic technique and specific instrument, applicator or device inserter, to insert a frameless, anchored device for intrauterine and intratubal delivery of bioactive substances for long-acting contraception and gynecological treatment. This is realized by the invention of a specially designed inserter allowing the passage through the narrow working channel of a specially designed hysteroscope for the precise insertion of an anchoring means, a non-biodegradable or biodegradable anchoring knot, or a hook, under direct vision in the fundal wall of the uterus, and to which a biological active component is attached which consists of a copper, copper-silver or another metallic ion-releasing agent, or a drug-eluting system for the release of a hormone or hormone-antagonist or other substance, active in the uterus as well as in the oviducts, and which can be hand-fixed to the hysteroscope by means of a thumbpiece fixed to the inserter tube to allow safe and controlled insertion. This particular insertion instrument is provided with several means to minimize deflation of the uterus during use, and a double release mechanism to allow proper placement and to minimize the risk of insertion failure. The intrauterine device (IUD) or intrauterine system (IUS), as described and inserted under vision through a hysteroscope, serves primarily for the insertion of precision, reversible, long-acting reproductive control (ReLARC™) devices and systems. The invention also covers the use of the device inserter with other similar endoscopes for the anchoring or implantation of other devices or drug releasing systems to other organs systems or tumors, including the gastrointestinal, urinary, respiratory, cardiovascular systems of mammals for the purpose of local and/or regional effects.

There are several possible modes of realization. According to one aspect the front end of the device inserter consists of a J-shape tip. The purpose of the tip is to secure the anchoring knot from being dislodged during shipping/storage by a tail fixed at the rear end/handle of the device inserter. Furthermore the design of the tip allows for a precise location and placement depth within the uterus.

The design of the inserter handle, consisting of metal or plastic or other suitable material, is such that it can be used with one hand for placement of an intrauterine device or system via hysteroscopy for contraceptive or gynecological treatment. This assembly, scope and inserter, could be an endoscope for insertion of a non-biodegradable or biodegradable anchoring knot or hook for anchoring bioactive substances to other organs including but not limited to gastrointestinal organs, lungs, esophagus, peritoneal cavity, bladder, cardiovascular, etc.

According to another aspect of the invention, the handle contains a release mechanism for the tail of the IUD/IUS which can be operated with one hand, right or left by activating a mechanism provided at the end of the handle.

According to another aspect of the invention, the instrument for inserting the IUD/IUS, consisting of an inner part with handle and an outer tube for the protection of the tip of the needle during insertion of the instrument in the uterus, is provided with a means to prevent leakage of air or water from the pre-filled uterine cavity.

According to yet another new characteristic of the invention, the IUS is string-shaped and completely flexible to allow easy adaptation with the hysteroscope, after assembly with the hysteroscope inserter, and is anchored in the fundus of the uterus.

According to yet another characteristic of the invention, the string-shaped IUD is provided with tubal extensions which release Cu and/or Ag ions in the Fallopian tubes and have a contraceptive function.

According to yet another characteristic of the invention, the string-shaped IUD is provided with a cervical extension delivering Cu and Ag ions in the cervix for additional contraceptive action and prevention of infection.

According to another characteristic of the invention, the cervical extension of the suture is coated with an electrospun polymer loaded with CuO and Ag nano- or microparticles. The anchoring and electrospun coated suture are connected to each other with a metal clip making the device visible on ultrasound.

According to another invention the fibers can release substances form a variety of agents including but not limited to hormones or anti-hormones.

According to yet another characteristic of the invention, the cervical extension of the suture, which is coated with an electrospun polymer, loaded or not, with CuO and Ag nano- or microparticles, is a coaxial fiber containing Cu and/or Ag micro or nanoparticles.

According to another embodiment of the invention, the tubal extensions are provided with a retention means or hook (such as 1 to 2 mm in size, to allow easy passage within a hysteroscope), visible on ultrasound, to fix the extensions into the fallopian tubes.

According to another aspect of the invention, the applicator to be used with the endoscope consists of disposable material.

DESCRIPTION OF THE DRAWINGS

These and other features of the insertion instrument with double release mechanism, one to unlock the handle, the other to release the tail of the IUD/IUS, will be more readily understood when referring to the description as well as the accompanying drawings which represent, merely by way of non-limitative examples, several embodiments of the invention, and in which.

DETAILED DESCRIPTION

Figure 1:
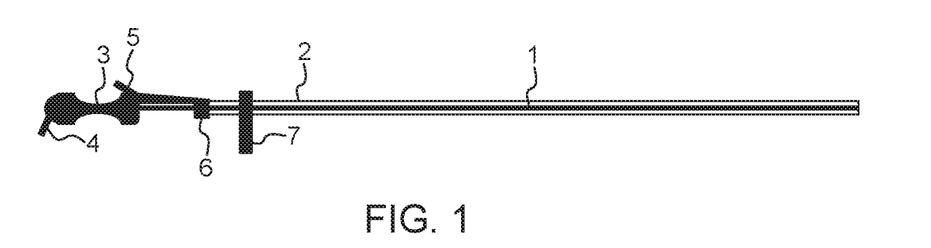
FIG. 1 is an applicator or a device-inserter consisting of an inner part and an outer tube. Both components are specifically designed for use in conjunction with a hysteroscope of limited dimensions or for blind insertion.

Referring to FIG. 1, the hysteroscopic applicator or device inserter consists of an inner part 1, an outer protecting (insertion) tube 2, a handle 3 and a release clip 4 to release the tail of the IUD/IUS. The handle 3 is connected with the insertion tube 2 by a release mechanism 5 provided with a connection ring 6, attached to the insertion tube 2, to release the tail of the IUD/IUS. A thumbpiece 7 is also fixed on the outer tube 2 to secure the applicator in a hysteroscope (not shown) in a pre-insertion position prior to inserting the IUD/IUS in the wall of the uterus under direct vision. The inner part 1 may be a flexible inner tube, and may be produced from metal. The outer insertion tube 2 may be a transparent plastic tube and may be flexible, allowing visibility of the IUD/IUS through the wall of the outer tube, and having a diameter thereby facilitating passage through the hysteroscope working channel. The inserter may be 10 cm to 75 cm long, and when used with a hysteroscope, the hysteroscope may be 1 to 2 cm shorter than the stylet to control a depth of insertion of an anchor of the IUD/IUS in the wall of the uterus under direct vision. The inserter is configured to pass through the hysteroscope working channel having a diameter between 1 and 2 mm. The handle 3 and/or the outer tube 2 may be color coded to aid in preventing inadvertent use of the inserter in the wrong hysteroscope.

Figure 2:
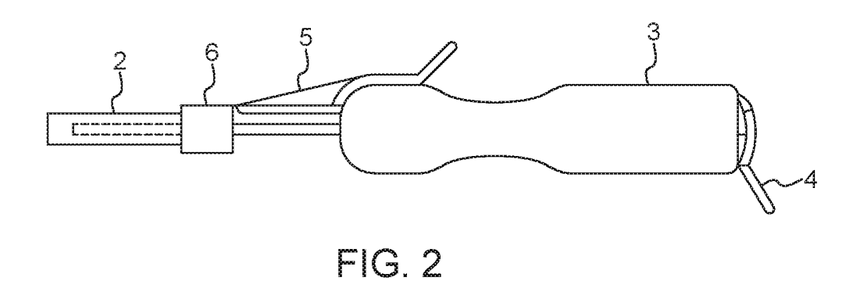
FIG. 2 is a side view of the handle showing the thread release mechanism and the mechanism to unlock the handle.
Figure 3:
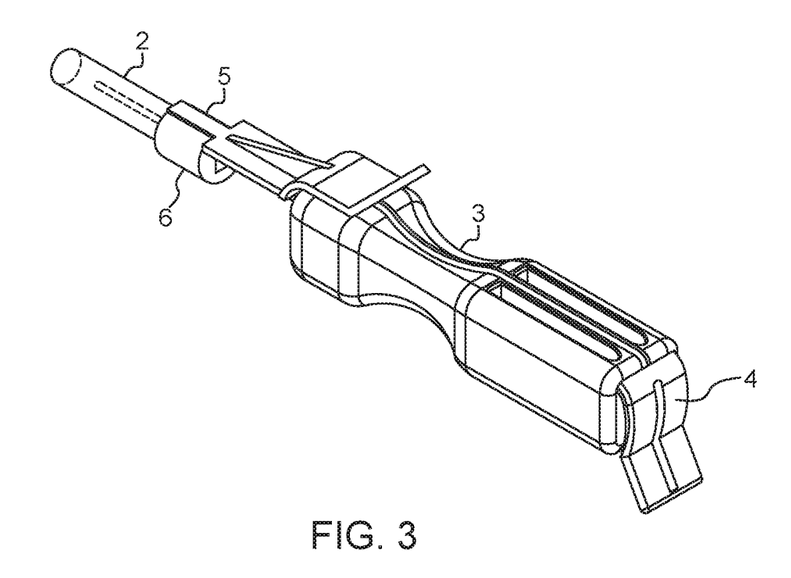
FIG. 3 is another view from above of the handle with release mechanism of the tail of the IUD/IUS at the end of the handle and release mechanism to release the handle which links it with the insertion tube.

FIG. 2 and FIG. 3 illustrate a preferred mode of realization of the invention in which the handle 3 with release clip 4 in locked mode is shown and which is connected with insertion tube 2 by release mechanism 5 connected on the one hand with a handle 3 and an insertion tube 2.

Figure 4:
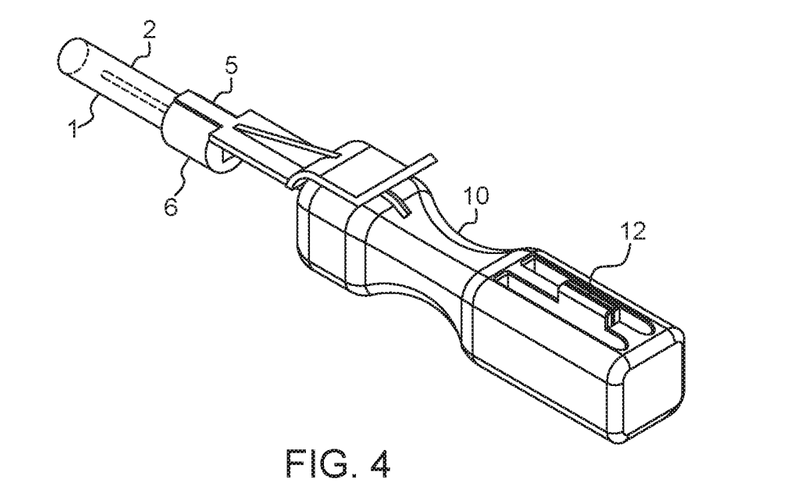
FIG. 4 is yet another view from above of the handle with release mechanism of the tail of the IUD/IUS situated on top of the handle and release mechanism to release the handle which links it with the insertion tube.

FIG. 4 illustrates another preferred mode of realization of the invention in which a handle 10 with slot 12 for fixation of the tail of the IUD/IUS is shown and release mechanism 5 in locked mode which is connected with insertion tube 2.

Figure 5:
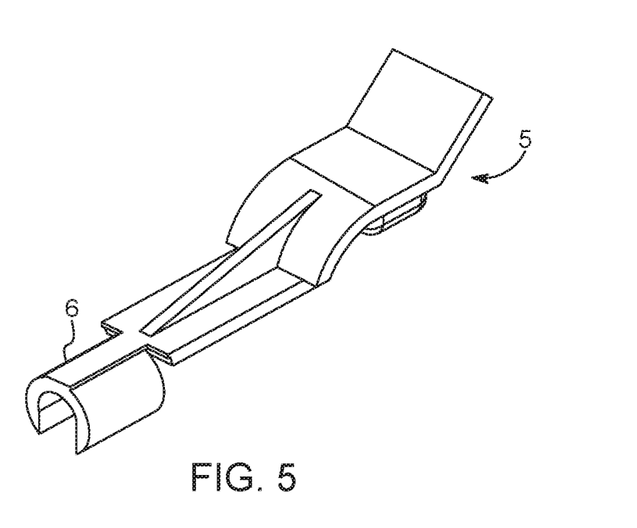
FIG. 5 is a view of the release mechanism to lock/unlock the handle which connects the handle with the insertion tube and which is provided with a narrow part (FIG. 5A) at the back end of the connecting piece to minimize leakage of water from the uterus during the procedure.
Figure 5A:
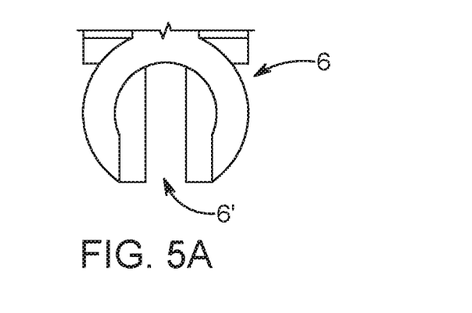

FIG. 5 is a view of the release mechanism 5, to lock/unlock the handle, which connects the handle with the insertion tube and which is provided with a narrow part 6' (FIG. 5A) at the end of the connecting piece 6 to minimize leakage of water from the uterus during the procedure.

Figure 6:
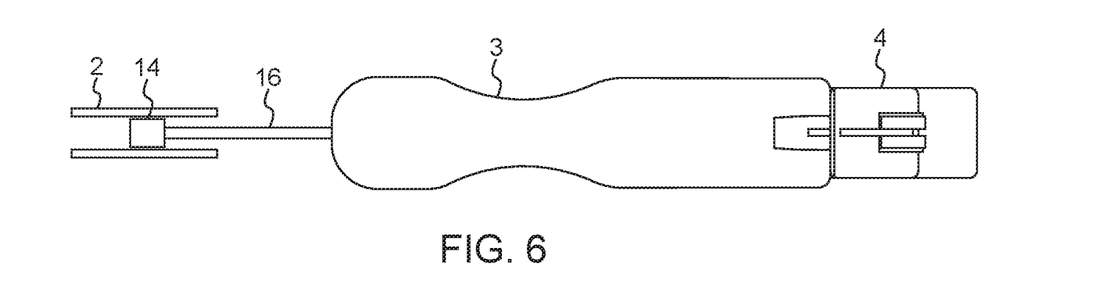
FIG. 6 is a view from below of the handle which shows the unlocked release mechanism at the end of the handle and in front, a tiny cylindrical element(FIG. 6A), fixed on the stylet which is molded in the handle, and which fits snugly in the inserter tube to minimize leakage of water flow from the uterus, and which is provided with an opening to allow the passage of the tail of the IUD/IUS.
Figure 6A:
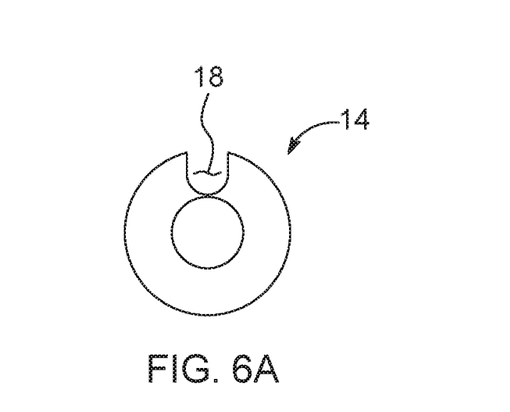

FIG. 6 is a view from below of the handle 3 which shows the unlocked release mechanism 4 at the end of the handle and in front, a tiny cylindrical element 14 (FIG. 6A) fixed on the stylet 16 which is molded in the handle, and which fits snugly in the insertion tube 2 to minimize leakage of fluid or air (such as water) flow from the uterus, and which is provided with an opening 18 on top to allow the passage of the tail of the IUD/IUS.

Figure 7:
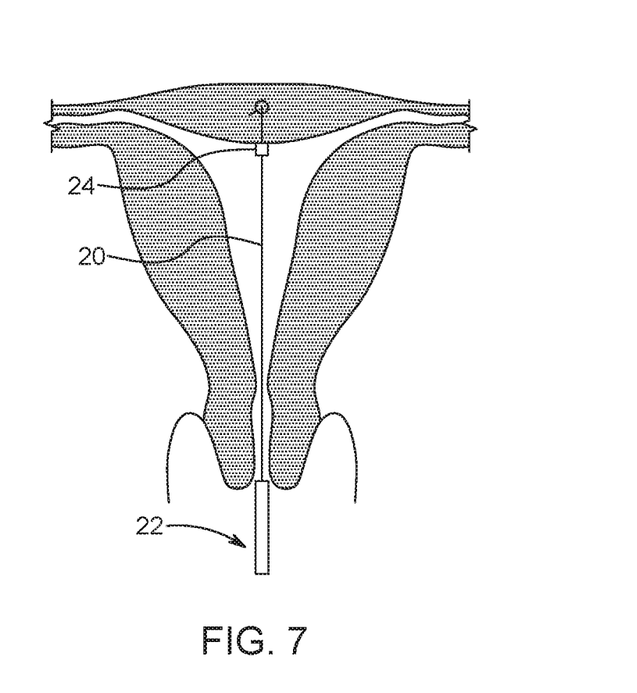
FIG. 7 is a polymeric drug delivery system, fixed to the top of the uterus, specially designed for insertion through a hysteroscope and which is loaded with metallic micro or nanoparticles for release of copper or silver ions in the uterine cavity.

FIG. 7 illustrates a preferred mode of realization of the invention in which a thin IUS 20 is illustrated, consisting of a polymeric drug delivery system, loaded with metallic micro or nanoparticles, inserted through the working channel of a hysteroscope 22 and of which the anchor is inserted in the fundus of the uterus with a thin hysteroscope inserter, in accordance with the invention. The thin fibrous delivery system, attached to the anchoring suture with a metal clip 24, is active in the uterus as well as in the cervix. This device is a multipurpose fiber extending in the cervix for both contraception and infection prevention. It has no rigid plastic body, making it a completely flexible unit.

Figure 8:
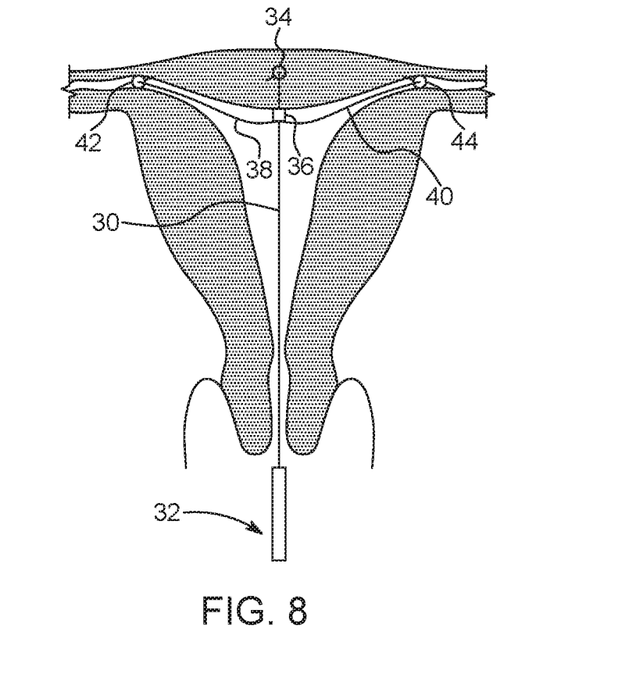
FIG. 8 is another polymeric drug delivery system, fixed to the top of the uterus, loaded with metallic micro or nanoparticles, specially designed for insertion through a hysteroscope and which has two extensions for insertion and fixation in the fallopian tubes.

FIG. 8 is another illustration of one of the preferred modes of realization of the invention in which a thin IUS 30 is illustrated, consisting of a polymeric drug delivery system, loaded with metallic micro or nanoparticles, inserted through the working channel of an office hysteroscope 32 and of which the anchor 34 is inserted in the fundus of the uterus with a thin hysteroscope inserter, in accordance with the invention. The device consists of a thin fibrous delivery system, attached to the anchoring suture with a metal clip 36, which is active in the uterus and cervix. This device is a multipurpose fiber extending in the cervix for both contraception and infection prevention. In addition, a similar multipurpose fibers 38 and 40 is also fixed in metal clip 36. Both tubal extensions are inserted in the tubes with a specially designed forceps and kept in place by anchoring means 42 and 44. The multipurpose IUS, with cervical and tubal extensions, has no rigid plastic body, making it a completely flexible unit to prevent traumatic lesions to the uterus.

Figure 9A:
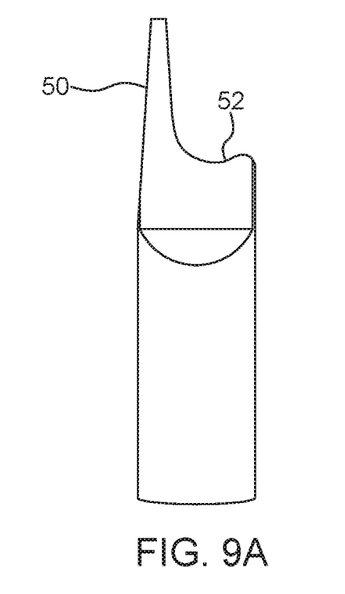
FIG. 9a and FIG. 9b are representations of the very small tip of the stylet to allow assembly with an IUD or IUS for insertion through a hysteroscope and fixation at the top of the uterus.
Figure 9B:
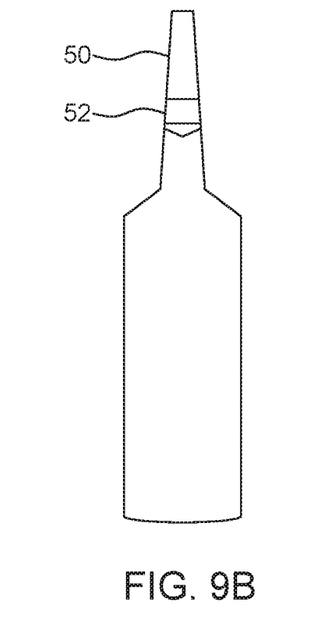

FIG. 9A and FIG. 9B show one mode of realization of a J-shape of the upper extremity of the inserter of which FIG. 9A is a side-view depicting the tip and shoulder 52 of the inserter; and FIG. 9B a front view equally depicting the tip 50 and shoulder 52 of the inserter. Other tip shapes are contemplated including t-, l-, u-, v-, or inverted t-shape. The invention further contemplates an intrauterine system comprising an IUD comprising two fibrous components, one fibrous component for extending from a top of a uterus into a cervical canal, the other fibrous component for extending in both fallopian tubes, both having a dimension between 1 and 2 mm, the intrauterine system further comprising the inserter, wherein the IUD is extended through the inserter and is configured to be active in the uterus as well as in the oviducts and is further configured to release ions from metallic micro or nanoparticles embedded in the fiber of one or both of the fibrous components into the uterine cavity and fallopian tubes, wherein the fiber can be co-axial or monolithic, or covered by electrospun material. The two fibrous components are provided with small deformations or hooks to retain them in place, and the metallic micro or nanoparticles consist of copper and/or silver.

The invention has been described and illustrated merely by way of example which is in no way restrictive. Numerous changes in its conception may be made without departing from the spirit of the invention.

The invention claimed is:

1. A disposable IUD/IUS inserter, for use in conjunction with a hysteroscope comprising an inner part comprising a stylet having a stylet tip for inserting an anchoring portion of an IUD/IUS into a fundal wall of a uterus; said inserter is further provided with:
   a handle connected to a rear end of said stylet;
   a tail release mechanism extending from a rear end of the handle, the tail release mechanism comprising a rounded portion extending about the rear end of the handle and a flat plate extending away at a decline from the rear end of the handle and the rounded portion, the tail release mechanism being configured to release a tail of the IUD/IUS;

an outer tube covering the stylet and sized to allow passage through a hysteroscope working channel, and a handle unlocking mechanism releasably connected to said outer tube and comprising a connecting ring partially surrounding the outer tube, the connecting ring has a narrow part at a back end of the connecting ring to reduce release of water from the uterus through the outer tube during insertion, the handle unlocking mechanism further comprising a flat plate rearward of the connecting ring and extending at an incline in the opposite direction of the declining flat plate of the tail release mechanism.

2. The inserter according to claim 1, wherein the outer tube comprises a transparent, flexible plastic tube, allowing visibility of the IUD/IUS through a wall of the outer tube, having a diameter thereby facilitating passage through the hysteroscope working channel, and is 1 to 2 cm shorter than the stylet to control a depth of insertion of an anchor of the IUD/IUS in the wall of the uterus under direct vision.

3. The inserter according to claim 2, wherein the outer tube is provided with a thumbpiece securely fixed onto the outer tube to secure the inserter in the hysteroscope working channel in a pre-insertion position prior to inserting the anchor in the wall of the uterus under direct vision.

4. An intrauterine system comprising an IUD comprising two fibrous components, one fibrous component for extending from a top of a uterus into a cervical canal, the other fibrous component for extending in both fallopian tubes, both having a dimension between 1 and 2 mm, the intrauterine system further comprising the inserter of claim 3, wherein the IUD is extended through the inserter and is configured to be active in the uterus as well as in the oviducts and is further configured to release ions from metallic micro or nanoparticles embedded in the fiber of one or both of the fibrous components into the uterine cavity and fallopian tubes, wherein the fiber can be co-axial or monolithic, or covered by electrospun material.

5. The system according to claim 4, wherein the two fibrous components are provided with small deformations or hooks to retain them in place.

6. The system according to claim 4, wherein the metallic micro or nanoparticles consist of copper and/or silver.

7. The inserter according to claim 1, wherein the inserter is configured to pass through the hysteroscope working channel having a diameter between 1 and 2 mm.

8. The inserter according to claim 1, further comprising a cylindrical element adjacent a front end of the handle which fits snugly into said outer tube to minimize leakage of fluid or air through the outer tube from the uterine cavity to prevent deflation of the uterus, wherein an opening is provided on an outer surface of the cylindrical element to allow passage of the tail of the IUD/IUS between the cylindrical element and an inner surface of the outer tube.

9. The inserter according to claim 1, wherein the stylet tip has a J-, t-, l-, u-, v- or inverted t-shape.

10. The inserter according to claim 1, wherein a length of the inserter is from 10 cm to 75 cm.

11. The inserter according to claim 1, wherein the tail release mechanism is a release clip extending outwardly from the handle.

12. The inserter according to claim 1, wherein the handle unlocking mechanism is separate from the handle.

* * * * *

UNITED STATES PATENT AND TRADEMARK OFFICE
CERTIFICATE OF CORRECTION

| | |
|---|---|
| PATENT NO. | : 11,672,691 B2 |
| APPLICATION NO. | : 15/750596 |
| DATED | : June 13, 2023 |
| INVENTOR(S) | : Dirk Wildemeersch |

It is certified that error appears in the above-identified patent and that said Letters Patent is hereby corrected as shown below:

In the Claims

Column 9, Line 20, Claim 2, delete "and is" and insert -- and which is --

Signed and Sealed this
Twenty-ninth Day of August, 2023

*Katherine Kelly Vidal*

Katherine Kelly Vidal
*Director of the United States Patent and Trademark Office*